United States Patent [19]

Cox et al.

[11] 3,961,072

[45] June 1, 1976

[54] PHENOXYPROPANOLAMINE THERAPEUTIC AGENTS

[75] Inventors: David Alexander Cox, Canterbury; John Christopher Danilewicz, Sandwich; Allan Leslie Ham, Broadstairs; John Edward Glyn Kemp, Canterbury; Michael Snarey, Sandwich, all of England

[73] Assignee: Pfizer Inc., New York, N.Y.

[22] Filed: Aug. 9, 1974

[21] Appl. No.: 496,288

Related U.S. Application Data

[60] Division of Ser. No. 345,726, March 28, 1973, Pat. No. 3,845,123, which is a continuation of Ser. No. 98,168, Dec. 14, 1970, abandoned.

[30] Foreign Application Priority Data

Dec. 17, 1969 United Kingdom............... 61414/69
May 20, 1970 United Kingdom............... 24360/70

[52] U.S. Cl. ............................................. 424/324
[51] Int. Cl.² ....................................... A61K 31/165
[58] Field of Search ................................... 424/324

[56] References Cited
UNITED STATES PATENTS

| | | | |
|---|---|---|---|
| 3,337,628 | 8/1967 | Smith et al. ......................... | 260/562 |
| 3,562,297 | 2/1971 | Howe et al. ......................... | 260/562 |
| 3,574,749 | 4/1971 | Howe et al. ......................... | 260/562 |

*Primary Examiner*—Jerome D. Goldberg
*Attorney, Agent, or Firm*—Connolly and Hutz

[57] ABSTRACT

A series of novel substituted phenoxypropylamine derivatives have been prepared by reacting the appropriate 1-phenoxy-2,3-epoxypropane compound with a suitable organic amine reagent. The resulting 1-phenoxy-3-alkylaminopropan-2-ols are useful in the field of chemotherapy as anti-angina agents. Preferred members include compounds having an acetamido group substituted on the phenyl ring of the phenoxy moiety. Alternate methods of preparation are also provided.

6 Claims, No Drawings

PHENOXYPROPANOLAMINE THERAPEUTIC AGENTS

CROSS REFERENCE TO RELATED APPLICATION

This application is a division of application Ser. No. 345,726 filed Mar. 28, 1973 now U.S. Pat. No. 3,845,123 which is a continuation of application Ser. No. 98,168 filed Dec. 14, 1970 and now abandoned.

BACKGROUND OF THE INVENTION

This invention relates to certain new and useful phenoxypropyl and phenylthiopropyl amine derivatives of principal interest to those in the field of chemotherapy. More particularly, it is concernred with various novel substituted 1-phenoxy-3-alkylaminopropan-2-ols and their non-toxic acid addition salts, which are of especial value in view of their anti-angina properties.

In the recent past, several attempts have been made by investigators in this particular field of therapy to obtain new and still better forms of agents and/or methods for the treatment of cardiac conditions like angina pectoris and 50 on. In many instances, these efforts have further involved the synthesis and testing of various new and heretofore unavailable compounds, particularly in the area of the propanolamines. For instance, R. Howe et al. in U.S. Pat. No. 3,408,387 disclose a series of amidoaryloxyalkanolamines in this category, including compounds like 1-(4-acetamidophenoxy)-3-(2-phenoxyethylamino)propan-2-ol, which are reported to be useful as antihypertensive agents, in addition to possessing $\beta$-adrenergic blocking properties. However, little is known about the effect of other alkanolamines in this area, such as those compounds which differ from the aforesaid prior art by having an addition polar group in the previously unsubstituted phenyl ring of the 2-phenoxyethylamino moiety.

SUMMARY OF THE INVENTION

In accordance with the present invention, it has now been rather surprisingly found that certain novel 1-phenoxy- and 1-phenylthio-3-alkylaminopropan-2-ol compounds are extremely useful when employed in the field of drug therapy as cardiospecific anti-angina agents. The novel compounds of this invention are all selected from the group consisting of phenoxypropanolamine bases of the formula:

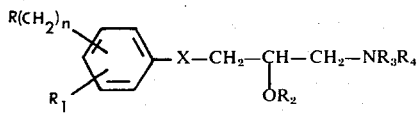

and the pharmaceutically acceptable acid addition salts thereof, wherein R is a member selected from the group consisting of alkanoylamino having from one to six carbon atoms, N-methyl-N-alkanoylamino and N-ethyl-N-alkanoylamino each having from two to six carbon atoms in the alkanoyl moiety, chloroacetylamino, trifluoroacetylamino, acryloylamino, benzoylamino, toluoylamino, chlorobenzoylamino, nitrobenzoylamino, furoylamino, phenylalkanoylamino having up to three carbon atoms in the alkanoyl moiety, succinoylimino, phthaloylimino, carbamoyl, N-monoalkylcarbamoyl and N,N-dialkylcarbamoyl each having up to three carbon atoms in the alkyl moiety, N-phenylcarbamoyl, N-phenylalkylcarbamoyl having up to three carbon atoms in the alkyl moiety and alkoxycarbonylamino having from one to six carbon atoms in the alkoxy moiety; $n$ is an integer of from 0 to 2; $R_1$ is a member selected from the group consisting of hydrogen, allyl, alkyl and alkoxy each having from one to six carbon atoms, fluorine, chlorine and bromine; $R_2$ is a member selected from the group consisting of hydrogen and alkanoyl having from two to six carbon atoms; $R_3$ is a member selected from the group consisting of hydrogen, alkyl having from one to six carbon atoms and phenylalkyl having up to three carbon atoms in the alkyl moiety; $R_4$ is a member selected from the group consisting of arylalkyl and aryloxyalkyl each having up to four carbon atoms in the alkyl moiety with said aryl group being chosen from the group consisting of alkanoylaminophenyl and alkanoylaminomethylphenyl each having from one to six carbon atoms in the alkanoyl moiety, carbamoylphenyl, carbamoylmethylphenyl, N-monoalkylcarbamoylphenyl and N,N-dialkylcarbamoylphenyl each having up to three carbon atoms in the alkyl moiety, N-phenylcarbamoylphenyl, and N-phenylalkylcarbamoylphenyl having up to three carbon atoms in the alkyl moiety; and X is oxygen or sulfur. These novel phenoxypropanolamine compounds all possess strong $\beta$-adrenergic blocking activity, particularly with respect to their effect on myocardial $\beta$-receptors rather than peripheral $\beta$-receptors (i.e., those affecting vascular, tracheal or bronchial tissue). They are therefore useful in the treatment of cardiac conditions, such as angina pectoris and cardiac arrhythmias, without adversely affecting blood pressure or lung or bronchial conditions in afflicted subjects.

Of especial interest in this connection are the preferred compounds of the present invention where $R(CH_2)_n$ in the aforesaid structural formula is specifically located at the 4-position of the phenyl ring and is preferably alkanoylamino or alkanoylaminomethyl as previously defined (and most preferably, it is acetamido or acetamidomethyl), $R_1$ is hydrogen or it is allyl or alkyl having from one to six carbon atoms at the 2-position of the phenyl ring, $R_2$ and $R_3$ are each hydrogen, $R_4$ is alkanoylaminophenoxyethyl having from one to six carbon atoms in the alkanoyl moiety (and most preferably, 4-acetamidophenoxyethyl), and X is oxygen. Typical member compounds of the preferred class include such 1-phenoxy-3-(2-phenoxyethylamino)propan-2-ols as 1-(4-acetamidophenoxy)-3-[2-(4-acetamidophenoxy)ethylamino]propan-2-ol, 1-(4-acetamidomethylphenoxy)-3-[2-(4-acetamidoxphenoxy)ethylamino]propan-2-ol, 1-(2-methyl-4-acetamidophenoxy)-3-[2-(4-acetamidophenoxy)ethylamino]propan-2-ol, 1-(2-methyl-4-acetamidomethylphenoxy)-3-[2-(4-acetamidophenoxy)ethylamino]propan-2 -ol and 1-(2-allyl-4-acetamidophenoxy)-3-[2-(4-acetamidophenoxy)ethylamino]propan-2-ol, respectively. These particular compounds are all highly potent as regards their selective $\beta$-adrenergic blocking activity, i.e., they show a high degree of selectivity for heart tissue as compared to lung tissue, etc., in addition to possessing the ability to block myocardial $\beta$-receptors to a very high degree.

DETAILED DESCRIPTION OF THE INVENTION

In accordance with the process employed for preparing the novel compounds of this invention, an appropriately substituted 1-phenoxy-2,3-epoxypropane or the thiophenoxy analog thereof is reacted with a suitable organic amine reagent of the formula $R_3R_4NH$, where $R_3$ and $R_4$ are each as previously defined to form the desired phenoxypropanolamine (or thiophenoxypropanolamine) final product, in which case $R_{1c}$ is always hydrogen. This particular reaction is normally carried out in the presence of a reaction-inert polar organic solvent such as a lower alkanol like methanol or ethanol, or a lower N,N-dialkylalkanoamide such as N,N-dimethylformamide, N,N-dimethylacetamide, N,N-diethylformamide and so on. In general, the reaction is conducted at a temperature that is in the range of from about 20°C. up to about 100°c. for a period of about 1 hour to about 7 days (e.g., 1 hour at 100°C. or 7 days at 20°C.). It should be noted that the epoxy starting materials employed in this reaction are, for the sake of time and convenience, most readily obtained from the corresponding phenols or thiophenols, as the case may be, by using standard organic procedures well-known to those skilled in the art for the reaction of phenols with 2,3-epoxypropyl chloride. For instance, the reaction can be carried out in aqueous alkali at ambient temperatures, followed by extraction into a suitable organic solvent such as dichloromethane and recovery of the desired product from said solvent extract by conventional means.

Alternate methods of preparation for the compounds of this invention involve (1) reacting a suitable organic amine reagent of the formula $R_3R_4NH$ with a chlorohydrin or bromohydrin or an ether thereof (where $R_2$ is alkyl rather than hydrogen) corresponding in structure to the 2,3-epoxide previously employed; and (2) reacting the appropriate phenoxy- or phenylthiopropanolamine reagent or an ether derivative thereof with a suitable alkyl chloride or bromide of the formula $R_4X$, wherein $R_4$ is defined as aforesaid and X is halogen like chlorine or bromine. In both instances, these particular routes are carried out by first dissolving the key reactants in a mutual solvent, such as methanol or ethanol, which must also preferably contain a suitable amount of alkali reagent like sodium bicarbonate or else excess amine reactant, and then heating the entire mixture together, while under reflux conditions, until the reaction is essentially complete in each case. Additionally, the same reaction can also be carried out in either (1) or (2) by simply heating the two reactants together in equimolar proportions when in the absence of a solvent.

To prepare compounds of the invention where $R_4$ is arylalkyl or aryloxyalkyl which contains a branched-chain alkyl moiety (e.g., an appropriately substituted 2-phenoxy-1-methylethyl group), a preferred method of synthesis involves condensing an appropriately substituted phenoxypropanolamine reagent where $R_4$ is hydrogen with a corresponding arylalkyl or aryloxyalkyl ketone (e.g. an appropriately substituted phenoxyacetone) to form the desired Schiff's base, which is thereafter hydrogenated in the presence of a catalyst like platinum or reduced with sodium borohydride to yield the desired 1-phenoxy-3-alkylaminopropan-2-ol final product as previously defined. In this way, a propanolamine starting material like 1-(4-acetamidophenoxy)-3-aminopropan-2-ol is converted to 1-phenoxy-3-alkylaminopropan-2-ol final products such as 1-(4-acetamidophenoxy)-3-[2-(2-acetamidophenoxy)-1-methylethylamino]propan-2-ol, 1-(4-acetamidophenoxy)-3-[2-(4-carbamoylphenoxy)-1-methylethylamino]propan-2-ol, 1-(4-acetamidophenoxy)-3-[2-(4-acetamidophenoxy)-1-methylethylamino]propan-2-ol and 1-(4-acetamidophenoxy)-3-[2-(2-carbamoylphenoxy)-1-methylethylamino]propan-2-ol in a most facile manner.

As regards phenoxypropanolamine compounds of the invention where R on the phenyl ring of the phenoxy or thiophenoxy moiety is specifically acylamino (e.g., acetamido and the like), these are alternately and most easily prepared by subjecting the corresponding nitro compounds (i.e., where R on the phenyl ring is nitro) to catalytic hydrogenation, followed by acylation of the resulting amino group to yield the desired carboxamido final product. In this way, the amino compound serves as an intermediate for the preparation of other final products of this invention that can subsequently be derived therefrom. For instance, acylation with acetic anhydride leads to the acetamido compounds, while the use of acryloyl chloride, on the other hand, affords the corresponding acryloylamino final products.

Needless to say, compounds of the invention in which $R_2$ is alkyl of from one to six carbon atoms (i.e., ether derivatives) can also be prepared from compounds of the invention where $R_2$ is simply hydrogen by merely subjecting the latter unsubstituted phenoxypropanolamine per se to conventional alkylation procedures well-known to those skilled in the art. In like manner, the esters of those compounds having free groups (where $R_2$ is again hydrogen) can also be prepared by conventional procedure, starting from the aforesaid phenoxypropanolamines per se and using standard esterification techniques to achieve the desired esters of this invention where $R_2$ is alkanoyl having from two to six carbon atoms, provided that $R_3$ is not hydrogen. On the other hand, to obtain an ester in which $R_3$ is hydrogen, one must first start with a compound in which $R_3$ is other than hydrogen and is preferably a blocking group, such as benzyl, which is easily removable without affecting the ester linkage.

Inasmuch as the phenoxypropanolamine compounds of this invention all possess at least one asymmetric center, they may exist in separated d- and l-optically active forms, as well as in racemic dl-mixtures necessarily produced by the various synthetic methods just previously described. The invention, of course, includes the d-, l- and racemic forms all well within its scope. For instance, an optically active isomer may be obtained by simply resolving the racemic mixture using standard techniques well-known to those skilled in the art, e.g., by fractional crystallization of an acid addition salt derived from an optically active acid.

Needless to say, compounds of the invention which have two asymmetric centers also exist as two racemic pairs of diastereoisomers, and these racemic pairs can generally be separated from one another using column chromatography and/or other standard techniques well-known to those skilled in the art. Here again, the invention includes well within its scope the separate pairs of isomers and mixtures thereof, as the d-, l- and racemic forms all as previously mentioned.

The pharmaceutically acceptable acid addition salts of the phenoxypropanolamine base compounds of this invention are prepared by simply treating the corresponding organic bases with mineral and organic acids which form non-toxic acid addition salts having pharmacologically acceptable anions, such as the hydrochloride, hydrobromide, hydriodide, sulfate or bisulfate, phosphate or acid phosphate, acetate, maleate, fumarate, lactate, tartrate, citrate, gluconate, saccharate, methanesulfonate, benzenesulfonate and p-toluenesulfonate salts.

As previously indicated, the phenoxypropanolamine compounds of this invention are of especial value therapeutically when employed as anti-angina agents, particularly in view of their ability to block myocardial β-adrenergic receptor sites in cardiac-afflicted subjects to a statistically significant degree. For instance, 1-(2-methyl-4-acetamidophenoxy)-3-[2-(4-acetamidophenoxy)ethylamino]propan-2-ol, a typical and preferred agent of the present invention, has been found to exert its highly selective β-adrenergic blocking effect in conscious dogs to a statistically significant degree, with respect to heart tissue, when given by the oral route of administration without showing any substantial signs of toxic side effects. The other compounds of this invention also cause similar results. Furthermore, all the herein described compounds of this invention can be administered by either the oral or parenteral routes of administration, for the present purposes at hand, without causing any significant untoward pharmacological side effects to occur in the subject to whom they are so administered. In general, these compounds are ordinarily administered at oral dosage levels ranging from about 0.05 mg. to about 4.0 mg. per kg. of body weight per day, although variations will necessarily occur depending upon the weight and condition of the subject being treated and the particular route of administration chosen.

In connection with the use of the phenoxypropanolamine compounds of this invention of the treatment of cardiac-afflicated subjects, it is to be noted that these compounds may be administered alone, but generally will be administered in combination with a pharmaceutical carrier. The carrier is normally selected with regard to the intended route of administration as well as standard pharmaceutical practice. For example, these compounds may be administered orally in the form of tablets containing excipients such as starch or lactose, or in capsules either alone or on admixture with excipients, or else in the form of elixirs or suspensions containing flavoring agents or coloring matter, etc. For purposes of parenteral administration, they are best used in the form of a sterile aqueous solution of a previously enumerated water-soluble acid addition salt, which solution may also contain sufficient saline or glucose to render the final composition isotonic. These particular aqueous solutions are especially suitable for intravenous, intramuscular and subcutaneous injection purposes.

The activity of the compounds of the present invention, as anti-angina agents, i.e., as selective β-adrenergic blockers, is determined by their ability to selectively block myocardial β-receptors rather than peripheral β-receptors as previously discussed, based on any one or more of the following standard biological/or pharmacological tests, viz., (1) by measuring and comparing the inhibition of catecholamine-induced changes is isolated guinea-pig atria and trachea; (2) by measuring and comparing suppression of tachycardia and relaxation of the trachea induced by isoprenaline in the anesthetized guinea-pig; (3) by measuring the suppression of the tachycardia induced by isoprenaline in the anesthetized cat or conscious dog, and (4) by measuring and comparing suppression of the stimulating action of isoprenaline on the adenyl cyclase enzyme present in rat heart and lung tissue.

In test (1), the isolated guinea-pig atria and trachea, in controlled physiological liquid environments, are stimulated electrically and the effects of adding increasing amounts of adrenaline to the liquid environment, on both the rate and force of contraction of the atria, and of isoprenaline on the degree of relaxation of the traches, are then measured. The test compound is then added to the liquid environment at various concentration levels, and the effects of adding adrenaline and isoprenaline, respectively, are measured once again. The concentrations of test compound which give a 50% inhibition of the effects of adrenaline and isoprenaline are then calculated, and taken as a measure of activity of the compound per se with regard to inhibition of myocardial and peripheral β-receptors, respectively.

In test (2), blood pressure, heart rate and pressure within a segment of the trachea of a guinea-pig anesthetized with sufficient sodium pentobarbitone to prevent spontaneous respiration are measured, while artificial respiration is maintained directly into the lung at a constant rate. Isoprenaline, at a standard dose of $0.5\mu g.$, is then injected intravenously to induce tachycardia and to cause relaxation of the trachea and lower blood pressure. The ability of the test compound to suppress the tachycardia, and/or antagonize the relaxation of the trachea, and/or inhibit the fall in blood pressure caused by the isoprenaline is then measured by repeating the procedure, but this time injecting the test compound prior to the isoprenaline administration.

In test (3), chloralosed cats are dosed with the test compound intravenously at levels ranging from 0.1 mg. to 1.0 mg. per kg. of body weight, respectively, and the effect of an isoprenaline challenge on heart rate is measured. Heart rates are recorded both before dosing and at a 30-minute period thereafter, and the cats are then given a subcutaneous challenge of isoprenaline. The degree of isoprenaline-induced tachycardia is recorded at 15-minute intervals. Conscious dogs are also employed in such tests, with the test compound being administered intravenously at dose levels ranging from 0.125 to 0.25 mg./kg. and orally at 0.5 to 4 mg./kg., respectively.

In test (4), homogenized rat heart in a standardized medium, with and without isoprenaline, is incubated with adenosine-5'-triphosphoric acid (ATP) labelled with tritium. The test compound is then added at various concentration levels to the homogenate containing the isoprenaline. After incubation at 30°C., cyclic-3',-5'-adenosine-monophosphoric acid (cyclic-AMP), containing a known proportion of carbon-14 labelled material, is added and the synthesis of cyclic-AMP by the adenyl cyclase enzyme is stopped by raising the temperature. Cyclic-AMP is then separated and purified, and the amount synthesized in each case by the enzyme is measured as its tritium to carbon-14 ratio. The concentration of test compound which gives a 50% inhibition of the stimulating effect of isoprenaline on cyclic-AMP synthesis is taken as a measure of its activity. In order to assess the degree of tissue selectivity of the agent, the procedure is repeated using homogenized rat lung and the results obtained in this manner are compared with those previously reported for the homogenized rat heart.

Although the physician will ordinarily decide the proper dosage range at which these compounds are to be administered to humans, it is expected that for the treatment in man of cardiac conditions, such as angina pectoris, the preferred compounds of the invention will generally be administered orally at a level in the range from 0.5 to 4.0 mg. per kg. per day, divided in 3 or 4 daily doses, and that dosages for intravenous administration will generally be about one-tenth of these in a single daily dose. Thus, for a typical adult patient af about 70 kg. body weight, individual tablets or capsules might contain from 10 to 50 mg. of active ingredient and intravenous dosages would ordinarily contain from 1.0 to 20 mg. of said ingredient, in either case, combined in a suitable vehicle or carrier.

EXAMPLE I

A solution consisting of 13 g. of 1-(4-acetamidophenoxy)-3-aminopropan-2-ol and 10 g. of 2-acetamidophenoxyacetone dissolved in 75 ml. of ethanol was heated under reflux for a period of 2 hours. Upon completion of this step, a catalytic amount (0.3 g.) of platinum oxide was added to the cooled mixture, and the latter was subsequently hydrogenated at 20°C. and 1,100 p.s.i. pressure of hydrogen. After the hydrogen uptake had ceased, the catalyst was removed by means of filtration and the filtrate subsequently evaporated in vacuo to afford a yellow semi-solid product. The latter material was then dissolved in chloroform and extracted with aqueous hydrochloric acid, followed by basification of the aqueous layer and re-extraction into chloroform prior to filtering. Upon subsequent evaporation of the latter solution in the same manner as before, there were obtained 15 g. of pure 1-(4-acetamidophenoxy)-3-[2-(2-acetamidophenoxy)-1-methylethylamino]propan-2-ol as the free base, which was thereafter converted to the corresponding fumarate salt. After one recrystallization from methanol-diethyl ether and another from isopropanol-diethyl ether, there were ultimately obtained 3.9 g. of 1-(4-acetamidophenoxy)-3-[2-(2-acetamidophenoxy)-1-methylethylamino]propan-2-ol hemifumarate hemihydrate as final product, m.p. 104°C.

Anal. Calcd. for $C_{22}H_{29}N_3O_5 \cdot 1/2C_4H_4O_4 \cdot 1/2H_2O$: C, 59.70; H, 6.68; N, 8.71. Found: C, 59.45; H, 6.58; N, 8.46.

EXAMPLE II

The procedure described in Example I was repeated, except that 4-carbamoylphenoxyacetone was employed as starting material in place of 2-acetamidophenoxyacetone, using the same molar proportions as before. In this particular case, the corresponding final product thus obtained was 1-(4-acetamidophenoxy)-3-[2-(4-carbamoylphenoxy)-1-methylethylamino]propan-2-ol, ultimately isolated as the oxalate salt, m.p. 142°C.

Anal. Calcd. for $C_{21}H_{27}N_3O_5 \cdot C_2H_2O_4$: C, 56.30; H, 5.94; N, 8.56. Found: C, 56.32; H, 6.24; N, 8.50,

EXAMPLE III

The procedure described in Example I was repeated except that 2-carbamoylphenoxyacetone was employed as starting material in place of the corresponding 2-acetamido compound, using the same molar proportions as before. In this particular case, the corresponding final product thus obtained was 1-(4-acetamidophenoxy)-3-[2-(2-carbamoylphenoxy)-1-methylethylamino]propan-2-ol, ultimately isolated as the hemifumarate hemihydrate, m.p. 97°–99°C.

Anal. Calcd. for $C_{21}H_{27}N_3O_5 \cdot 1/2C_4H_4O_4 \cdot 1/2H_2O$: C, 58.80; H, 6.45; N, 9.05. Found: C, 59.16; H, 6.52; N, 8.95.

EXAMPLE IV

The procedure described in Example I was repeated exactly, except that 4-acetamidophenoxyacetone was employed as starting in place of the corresponding 2-acetamido compound. In this particular case, the corresponding final product thus obtained was 1-(4-acetamidophenoxy)-3-[2-(4-acetamidophenoxy)-1-methylethylamino]propan-2-ol, isolated as the free base, m.p. 165°-167°C.

Anal. Calcd. for $C_{22}H_{29}N_3O_5$: C, 63.59; H, 7.04; N, 10.11. Found: C, 63.88; H, 6.91; N, 10.31.

EXAMPLE V

A mixture consisting of 5.3 g. of 1-(4-acetamidophenoxy)-3-aminopropan-2-ol and 2.0 g. of 1-bromo-2-(4-acetamidophenoxy)ethane was heated at 140°C. for a period of 3 hours. At the end of this time, the resultant solid material formed from the reaction mixture was suspended in aqueous sodium carbonate solution, filtered and the resulting filter cake recrystallized once from water. After a further recrystallization from ethanol, there was ultimately obtained 0.25 g. of 1-(4-acetamidophenoxy)-3-[2-(4-acetamidophenoxy)-ethylamino]propan-2-ol, m.p. 193°-194°C.

Anal. Calcd, for $C_{21}H_{27}N_3O_5$: C, 62.82; H, 6.78; N, 10.47. Found: C, 62.33; H, 6.76; N, 10.32.

EXAMPLE VI

The procedure described in Example V was repeated except that 1-bromo-2-(2-carbamoylphenoxy)ethane was employed as starting material in place of 1-bromo-2-(2-acetamidophenoxy)ethane, using the same molar proportions as before. In this particular case, the corresponding final product thus obtained was 1-(4-acetamidophenoxy)-3-[2-(2-carbamoylphenoxy)ethylamino]propan-2-ol, ultimately isolated at the hemifumarate salt, m.p. 123°C.

Anal. Calcd. for $C_{22}H_{31}N_3O_5 \cdot 1/2C_4H_4O_4$: C, 59.31; H, 6.12; N, 9.43. Found: C, 59.01; H, 6.06; N, 6.45.

EXAMPLE VII

A solution consisting of 5.6 g. of 1-(4-acetamidophenoxy)-2,3-epoxypropane and 4.9 g. of 2-(4-carbamoylphenoxy)ethylamine dissolved in 100 ml. of ethanol was stirred at ambient temperatures for a period of 3 days. At the end of this time, the resulting precipitate was recovered from the mixture by means of suction filtration and recrystallized from aqueous ethanol to afored 5.4 g. of pure 1-(4-acetamidophenoxy)-3-[2-(4-carbamoylphenoxy)ethylamino]propan-2-ol in the fomr of a white crystalline solid, m.p. 175°-177°C.

Anal. Calcd. for $C_{20}H_{25}N_3O_5$: C, 62.00; H, 6.50; N, 10.85 Found: C, 61,83; H, 6.39; N, 11.18.

EXAMPLE VIII

The procedure described in Example VII was repeated to prepare the following 1-phenoxy-3-(2-phenoxyethylamino)propan-2-ol compounds, starting from the appropriate 1-phenoxy-2,3-epoxypropane and the corresponding 2-phenoxyethylamine reagent in each case:

1-(4-acetamidophenoxy)-3-[4-acetamidophenoxy)ethylamino]propan-2-ol, m.p. 198°–200°C.
1-(4-propionamidophenoxy)-3-[2-(4-carbamoylphenoxy)ethylamino]propan-2-ol, m.p. 187°–189°C.
1-(4-propionamidophenoxy-3-[2-(4-acetamidophenoxy)ethylamino]propan-2-ol, m.p. 203°C.
1-(2-methyl-4-acetamidophenoxy)-3-[2-(4-acetamidophenoxy)ethylamino]propan-2-ol, m.p. 178°–180°C.
1-(4-acetamidomethylphenoxy)-3-[2-(4-acetamidophenoxy)ethylamino]propan-2-ol, m.p. 176°–177°C.
1-(4-n-butyramidophenoxy)-3-[2-(4-acetamidophenoxy)ethylamino]propan-2-ol, m.p. 206°–207°C.
1-(3-methyl-4-acetamidophenoxy)-3-[2-(4-acetamidophenoxy)ethylamino]-propan-2-ol, m.p. 144°–146°C.
1-(4-carbamoylmethylphenoxy)-3-[2-(4-acetamidophenoxy)ethylamino]propan-2-ol, m.p. 190°–192°C.
1-(4-isobutyramidophenoxy)-3-[2-(4-acetamidophenoxy)ethylamino]propan-2-ol, m.p. 219°–220°C.
1-(2-methyl-4-acetamidophenoxy)-3-[2-(4-carbamoylphenoxy)ethylamino]-propan-2ol, m.p. 181°–182°C.
1-[4-(2-ethoxycarbonylamino)phenoxy]-3-[2-(4-acetamidophenoxy)ethylamino]-propan-2-ol, m.p. 166°–168°C.
1-[4-(2-acetamidoethyl)phenoxy]-3-[2-(4-carbamoylphenoxy)ethylamino]-propan-2-ol, m.p. 170°–173°C.
1-(3-methyl-4-acetamidophenoxy)-3-[2-(4-carbamoylphenoxy)ethylamino]-propan-2-ol, m.p. 168°–171°C.
1-[4-(2-ethoxycarbonylamino)-phenoxy]-3-[2-(4-carbamoylphenoxy)ethylamino]-propan-2-ol, m.p. 176°–178°C.
1-[4-(N-methylcarbamoyl)phenoxy]-3-[2-(4-acetamidophenoxy)ethylamino]-propan-2-ol monohydrate, m.p. 196°–198°C.
1-[4-(2-acetamidoethyl)phenoxy]-3-[2-(4-acetamidophenoxy)ethylamino]-propan-2-ol, m.p. 174°–175°C.
1-(4-methoxycarbonylamino)phenoxy-3-[2-(4-acetamidophenoxy)ethylamino]-propan-2-ol, m.p. 195°–197°C.
1-(2-methoxy-4-acetamidomethylphenoxy)-3-[2-(4-carbamoylphenoxy)ethylamino]propan-2-ol, m.p. 162°–164°C.
1-[4-(N-methylacetamidophenoxy)]-3-[2-(4-acetamidophenoxy)ethylamino]propan-2-ol, 77°–80°C.
1(4-acetamidomethylphenoxy)-3-[2-(4-carbamoylphenoxy)ethylamino]propan-2-ol, m.p. 177°C.
1-(3-acetamidomethylphenoxy)-3-[2-(4-carbamoylphenoxy)ethylamino]propan-2-ol, m.p. 142°–144°C.
1-(4-carbamoylmethylphenoxy)-3-[2-(4-carbamoylphenoxy)ethylamino]propan-2-ol, m.p. 194°–196°C.
1-(4-acetamidophenoxy)-3-[2-(4-propionamidophenoxy)ethylamino]propan-2-ol, m.p. 204°–205°C.
1-[4-(N-methylcarbamoyl)phenyl]-3-[2-(4-carbamoylphenoxy)ethylamino]propan-2-ol, m.p. 176°–177°C.
1-(4-acetamidophenoxy)-3-[2-(3-methyl-4-acetamidophenoxy)ethylamino]-propan-2-ol, m.p. 143°–114°C.
1-(4-propionamidomethylphenoxy)-3-[2-(4-acetamidophenoxy)ethylamino]-propan-2-ol, m.p. 171°–173°C.
1-(4-formamidophenoxy)-3-[2-(4-acetamidophenoxy)ethylamino]propan-2-ol, m.p. 153°–155°C.
1-(2-carbamoylphenoxy)-3-[2-(4-carbamoylphenoxy)ethylamino]propan-2-ol, m.p. 178°–180°C.
1-(4-acetamidomethylphenoxy)-3-[2-(4-carbamoylmethylphenoxy)ethylamino]-propan-2-ol, mp. 190°–191°C.
1-(2-acetamidophenoxy)-3-[2-(4-acetamidophenoxy)ethylamino]propan-2-ol, m.p. 159°–160°C.
1-(4-formamidomethylphenoxy)-3-[2-(4-acetamidophenoxy)ethylamino]propan-2-ol, m.p. 158°–160°C.
1-(4-acetamidomethylphenoxy)-3-[2-(2-acetamidophenoxy)ethylamino]propan-2-ol, m.p. 165°–166°C.
1-(2-methyl-4-acetamidomethyl)-3-[2-(4-acetamidophenoxy)ethylamino]propan-2-ol monohydrate, m.p. 104°–106°C.
1-(4-acetamidophenoxy)-3-[2-(4-carbamoylmethylphenoxy)ethylamino]propan-2-ol, m.p. 196°–197°C.
1-(2-methoxy-4-acetamidomethylphenoxy)-3-[2-(4acetamidophenoxy)ethylamino]propan-2-ol, m.p. 150°–152°C.
1-(4-acetamidophenoxy)-3-[2-(4-acetamidomethylphenoxy)ethylamino]propan-2-ol, m.p. 171°–173°C.
1-(4-acetamidomethylphenoxy)-3-[2-(4-acetamidomethylphenoxy)ethylamino]-propan-2-ol, m.p. 187°–188°C.
1-(2-allyl-4-acetamidophenoxy)-3-[2-(4-acetamidophenoxy)ethylamino]propan-2-ol, m.p. 147°–149°C.
1-(4-acetamidomethylphenoxy)-3-[2-(4-propionamidophenoxy)ethylamino]propan-2-ol, m.p. 185°–187°C.
1-(4-carbamoylphenoxy)-3-[2-(4-acetamidophenoxy)ethylamino]propan-2-ol, m.p. 138°–141°C.
1-(2-chloro-4-acetamidophenoxy)-3-[2-(4-acetamidophenoxy)ethylamino]propan-2-ol, m.p. 186°–188°C.
1-(4-acetamidophenoxy)-3-[2-(2-acetamidophenoxy)ethylamino]propan-2-ol, m.p. 152°–154°C.
1-(4-acetamidophenoxy)-3-[2-(4-formamidophenoxy)ethylamino]propan-2-ol, m.p. 154°–156°C.

EXAMPLE IX

The following 1-phenoxy-3-phenoxyalkylaminopropan-2-ol compounds are prepared according to the procedure of Example VII, starting from the appropriate 1-phenoxy-2,3-epoxypropane and the corresponding phenoxyalkylamine reagent in each instance:

$$R(CH_2)_n\text{-}C_6H_3(R_1)\text{-}O\text{-}CH_2\text{-}CH(OH)\text{-}CH_2\text{-}NHR_4$$

| R | n | $R_1$ | $R_4$ |
|---|---|---|---|
| 2-HCONH | two | H | 4-CH$_3$CONHC$_6$H$_4$O(CH$_2$)$_4$ |
| 3-n-C$_5$H$_{11}$CONH | zero | H | 2-H$_2$NCOC$_6$H$_4$O(CH$_2$)$_4$ |
| 4-HCONH | zero | 2-allyl | 3-H$_2$NCOC$_6$H$_4$O(CH$_2$)$_4$ |
| 3-n-C$_5$H$_{11}$CONH | two | 4-allyl | 4-C$_2$H$_5$CONHC$_6$H$_4$O(CH$_2$)$_4$ |
| 2-n-C$_5$H$_{11}$CONH | zero | 3-CH$_3$ | 4-H$_2$NCOC$_6$H$_4$O(CH$_2$)$_4$ |
| 3-HCONH | two | 4-n-C$_6$H$_{13}$ | 2-CH$_3$CONHC$_6$H$_4$O(CH$_2$)$_4$ |
| 4-H$_2$NCO | zero | H | 4-n-C$_5$H$_{11}$CONHC$_6$H$_4$O(CH$_2$)$_4$ |
| 2-H$_2$NCO | two | H | 3-H$_2$NCOC$_6$H$_4$O(CH$_2$)$_4$ |
| 4-n-C$_3$H$_7$NHCO | two | H | 2-CH$_3$CONHC$_6$H$_4$O(CH$_2$)$_4$ |
| 3-CH$_3$NHCO | zero | H | 4-H$_2$NCOC$_6$H$_4$O(CH$_2$)$_4$ |
| 2-CH$_3$OCONH | two | H | 3-C$_2$H$_5$CONHC$_6$H$_4$O(CH$_2$)$_4$ |
| 4-n-C$_6$H$_{13}$OCONH | zero | H | 2-H$_2$NCOC$_6$H$_4$O(CH$_2$)$_4$ |
| 3-HCONH | two | H | 4-n-C$_5$H$_{11}$CONHC$_6$H$_4$O(CH$_2$)$_2$ |
| 2-n-C$_3$H$_{11}$CONH | zero | H | 3-HCONHC$_6$H$_4$O(CH$_2$)$_2$ |
| 4-HCONH | zero | H | 3-H$_2$NCOC$_6$H$_4$O(CH$_2$)$_2$ |
| 3-n-C$_3$H$_{11}$CONH | two | H | 4-H$_2$NCOC$_6$H$_4$O(CH$_2$)$_2$ |
| 2-HCONH | two | 4-allyl | 4-HCONHC$_6$H$_4$O(CH$_2$)$_2$ |

-continued

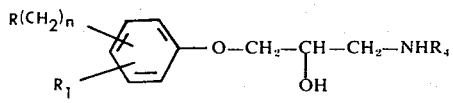

| R | n | R₁ | R₄ |
|---|---|---|---|
| 4-n-C₅H₁₁CONH | zero | 2-allyl | 2-n-C₅H₁₁CONHC₆H₄O(CH₂)₂ |
| 4-HCONH | zero | 2-CH₃ | 4-n-C₅H₁₁CONHC₆H₄O(CH₂)₂ |
| 3-n-C₅H₁₁CONH | two | 5-n-C₆H₁₃ | 2-HCONHC₆H₄O(CH₂)₂ |
| 3-HCONH | two | 4-n-C₆H₁₃ | 3-H₂NCOC₆H₄O(CH₂)₂ |
| 2-n-C₅H₁₁CONH | zero | 5-CH₃ | 4-H₂NCOC₆H₄O(CH₂)₂ |
| 4-H₂NCO | two | H | 4-CH₃CONHC₆H₄O(CH₂)₂ |
| 4-CH₃CONH | two | 2-allyl | 4-CH₃CONHC₆H₄O(CH₂)₂ |
| 4-CH₃CONH | two | 2-n-C₆H₁₃ | 4-CH₃CONHC₆H₄O(CH₂)₂ |
| 4-HCONH | two | H | 4-CH₃CONHC₆H₄O(CH₂)₂ |
| 4-n-C₅H₁₁CONH | zero | H | 4-CH₃CONHC₆H₄O(CH₂)₂ |
| 4-HCONH | one | 2-allyl | 4-CH₃CONHC₆H₄O(CH₂)₂ |
| 4-n-C₅H₁₁CONH | zero | 2-allyl | 4-CH₃CONHC₆H₄O(CH₂)₂ |
| 4-HCONH | one | 2-CH₃ | 4-CH₃CONHC₆H₄O(CH₂)₂ |
| 4-n-C₅H₁₁CONH | two | 2-CH₃ | 4-CH₃CONHC₆H₄O(CH₂)₂ |

EXAMPLE X

A solution consisting of 12 g. of 1-(3-nitrophenoxy)-3-[2-(4-carbamoylphenoxy)ethylamino]propan-2-ol (m.p. 127°–129°C.) dissolved in 1000 ml. of methanol was subjected to catalytic hydrogenation over 0.3 g. of platinum oxide at room temperature (~25°C.) and 50 p.s.i. pressure of hydrogen [the 3-nitro starting material was prepared according to the procedure of Example VII from 1-(3-nitrophenoxy)-2,3-epoxypropane and 2-(4-carbamoylphenoxy)ethylamine]. Upon completion of this step, the resultant mixture was filtered and the clear filtrate thereafter evaporated to dryness while under reduced pressure to afford a white residual solid. Recrystallization of the latter material from methanol then gave pure 1-(3-aminophenoxy)-3-[2-(4-carbamoylphenoxy)ethylamino]propan-2-ol, m.p. 149°–157°C.

An aqueous mixture consisting of 10 g. of 1-(3-aminophenoxy)-3-[2-(4-carbamoylphenoxy)ethylamino]propan-2-ol in 150 ml. of water was adjusted to pH 4–5 with dilute hydrochloric acid and then stirred vigorously for several minutes in order to effect complete solution. At this point, 3 g. of acetic anhydride were added to the mixture in a dropwise manner and the pH of the resulting solution was simultaneously maintained within the aforestated pH range by means of dilute aqueous sodium hydroxide. After further stirring the spent reaction mixture for a period of 1 hour, it was subsequently basified with additional dilute aqueous sodium hydroxide solution and the resulting solid precipitate with formed at this point was thereafter collected by means of suction filtration to give 1-(3-acetamidophenoxy)-3-[2-(4-carbamoylphenoxy)ethylamino]propan-2-ol as a white crystalline base, m.p. 164°–165°C. The analytical sample was then recrystallized from aqueous ethanol, but the melting point remained constant.

Anal. Calcd. for $C_{20}H_{25}N_3O_5$: C, 62.00; H, 6.50; N, 10.85. Found: C, 61.82; H, 6.44; N, 10.74.

EXAMPLE XI

The procedure described in Example X was repeated except that 1-(3-nitrophenoxy)-3-[2-(4-acetamidophenoxy)ethylamino]propan-2-ol (m.p. 107°–109°C.) was employed as starting material instead of 1-(3-nitrophenoxy)-3-[2-(4-carbamoylphenoxy)ethylamino]propan-2-ol, using the same molar proportions as before with respect to the key acylation step. In this particular case, 1-(3-nitrophenoxy)-3-[2-(4-acetamidophenoxy)ethylamino]propan-2-ol [prepared according to Example VII from 1-(3-nitrophenoxy)-2,3-epoxypropane and 2-(4-acetamidophenoxy)ethylamine] was converted to 1-(3-aminophenoxy)-3-[2-(4-acetaminophenoxy)ethylamino]propan-2-ol which, in turn, gave 1-(3-acetamidophenoxy)-3-[2-(4-acetamidophenoxy)ethylamino]propan-2-ol on treatment with acetic anhydride. The product was ultimately isolated as the hydrochloride salt, m.p. 237°–239°C.

Anal. Calcd. for $C_{21}H_{27}N_3O_5 \cdot HCl$: C, 57.57; H, 6.64; Cl, 8.08; N, 9.60. Found: C, 57.53; H, 6.77; Cl, 8.19; N, 9.33.

EXAMPLE XII

The procedure described in Example X was repeated again except that 1-(4-nitrophenoxy)-3-[2-(4-acetamidophenoxy)ethylamino]propan-2-ol (m.p. 179°–181°C.) was employed as starting material instead of 1-(3-nitrophenoxy)-3-[2-(4-carbamoylphenoxy)ethylamino]propan-2-ol and acryloyl chloride was the acylating agent of choice rather than acetic anhydride (using the same molar proportions, of course). In this particular case, 1-(4-nitrophenoxy-3-[2-(4-acetamidophenoxy)ethylamino]propan-2-ol [prepared according to Example VII from 1-(4-nitrophenoxy)-2,3-epoxypropane and 2-(4-acetamidophenoxy)ethylamine] was converted to 1-(4-aminophenoxy)-3-[2-(4-acetamidophenoxy)ethylamino]propan-2-ol which, in turn, gave 1-(4-acryloylamidophenoxy)-3-[2-(4-acetamidophenoxy)ethylamino]propan-2-ol on treatment with acryloyl chloride. The product was ultimately isolated as the hydrochloride salt, m.p. 241°–243°C.

Anal. Calcd. for $C_{22}H_{27}N_3O_5 \cdot HCl$: C, 58.73; H, 6.27; N, 9.43. Found: C, 58.62; H, 6.09; N, 9.17.

EXAMPLE XIII

The following 1-phenoxy- and 1-phenylthio-3-alkylaminopropan-2-ol compounds are prepared by employing the procedures described in the previous examples, starting from readily available materials in each instance:

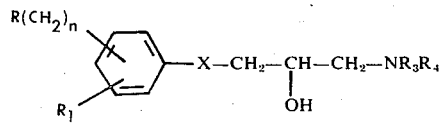

| R | n | R₁ | X | R₃ | R₄ |
|---|---|---|---|---|---|
| 3-HCONH | zero | 4-(n-C₆H₁₃) | O | H | 3-CH₃CONHC₆H₄(CH₂)₄ |
| 4-n-C₅H₁₁CONH | two | 3-allyl | O | CH₃ | 2-HCONHC₆H₄O(CH₂)₃ |

-continued

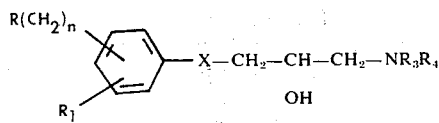

| R | n | R₁ | X | R₃ | R₄ |
|---|---|---|---|---|---|
| 2-HCONCH₃ | one | H | S | C₂H₅ | 4-n-C₅H₁₁CONHC₆H₄CH₂ |
| 3-n-C₅H₁₁CONCH₃ | zero | 4-Cl | O | C₆H₅CH₂ | 4-C₂H₅CONHC₆H₄O(CH₂)₄ |
| 4-HCONC₂H₅ | two | 3-Br | O | CH₃ | 3-HCONHCH₂C₆H₄O(CH₂)₂ |
| 4-n-C₅H₁₁CONC₂H₅ | zero | 2-F | S | n-C₆H₁₃ | 2-CH₃CONHCH₂C₆H₄(CH₂)₄ |
| 2-ClCH₂CONH | one | H | O | C₆H₅(CH₂)₂ | 4-H₂NCOCH₂C₆H₄O(CH₂ )₃ |
| 3-CF₃CH₂CONH | one | 5-CH₃ | S | H | 2-CH₃NHCOC₆H₄(CH₂)₄ |
| 4-CH₂=CHCONH | zero | 2-n-C₄H₉ | O | n-C₃H₇ | 3-H₂NCOC₆H₄O(CH₂)₂ |
| 2-C₆H₅CONH | two | H | O | H | 4-n-C₃H₇NHCOC₆H₄OCH₂ |
| 4-p-CH₃C₆H₄CONH | one | 2-allyl | S | H | 3-(CH₃)₂NCOC₆H₄O(CH₂)₄ |
| 3-o-ClC₆H₄CONH | zero | H | O | iso-C₃H₇ | 4-(n-C₃H₇)₂NCOC₆H₄CH₂ |
| 4-m-NO₂C₆H₄CONH | zero | H | O | C₆H₅(CH₂)₃ | 2-C₆H₅NHCOC₆H₄O(CH₂)₃ |
| 3-(2-furoylamino) | one | H | O | n-C₄H₉ | 4-C₆H₅(CH₂)₃NHCOC₆H₄(CH₂)₂ |
| 2-C₆H₅CH₂CONH | two | 4-Br | S | CH₃ | 3-CH₃CONHC₆H₄O(CH₂)₄ |
| 4-C₆H₅(CH₂)₃CONH | zero | H | O | H | 2-n-C₅H₁₁CONHC₆H₄O(CH₂)₃ |
| 3-succinoylimino | zero | H | O | H | 4-HCONHC₆H₄CH(CH₃)₂ |
| 4-phthaloylimino | one | 2-OCH₃ | S | C₂H₅ | 2-HCONHCH₂C₆H₄(CH₂)₄ |
| 2-H₂NCO | two | 5-Cl | O | H | 4-n-C₅H₁₁CONHCH₂C₆H₄OCH₂ |
| 3-CH₃NHCO | zero | H | S | H | 3-H₂NCOCH₂C₆H₄CH(CH₃)CH₂ |
| 2-(CH₃)₂NCO | zero | 4-OC₆H₁₃(n) | O | H | 3-CH₃NHCOC₆H₄O(CH₂)₃ |
| 3-(n-C₃H₇)₂NCO | two | H | S | n-C₃H₇ | 2-(CH₃)₂NHCOC₆H₄(CH₂)₄ |
| 2-C₆H₅NHCO | one | H | O | CH₃ | 3-iso-C₃H₇NHCOC₆H₄(CH₂)₄ |
| 4-C₆H₅(CH₂)₃NHCO | zero | 2-C₂H₅ | S | H | 2-C₆H₅CH₂NHCOC₆H₄OCH₂ |
| 2-CH₃OCONH | two | 4-allyl | S | H | 4-C₆H₅NHCOC₆H₄CH(CH₃)CH₂ |
| 4-C₆H₅ (CH₂)₃NHCO | zero | 3-F | O | C₂H₅ | 4-C₂H₅CONHCH₂C₆H₄O(CH₂)₂ |
| 4-iso-C₃H₇NHCO | one | 3-Br | O | C₆H₅CH₂ | 4-H₂NCOCH₂C₆H₄O(CH₂)₂ |

EXAMPLE XIV

Two grams of 1-(2-methyl-4-acetamidophenoxy)-3-{N-[2-(4-acetamidophenoxy)ethyl]-N-benzylamino} propan-2-ol are added to 20 ml. of anhydrous pyridine, followed by the immediate addition of 8.0 g. of acetic anhydride to the mixture with stirring. The resulting solution is then refluxed for a period of five minutes, cooled and subsequently poured into 50 ml. of ice water. The latter aqueous soltuion is then basified with 2N aqueous sodium hydroxide solution and extracted with chloroform, and the chloroform extract is thereafter washed with water and dried over anhydrous sodium sulfate prior to concentration in vacuo. The crude product obtained in this manner is then recrystallized from ethanol to afford pure 1-(2-methyl-4-acetamidophenoxy)-3-{N-[2-(4-acetamidophenoxy)ethyl]-N-benzylamino}-2-acetoxypropane. On subsequent treatment with hydrogen in the presence of palladium-on-carbon, the latter compound then gave 1-(2-methyl-4-acetamidophenoxy)-3-[2-(4-acetamidophenoxy)ethylamino]-2-acetoxypropane.

In like manner, 1-(4-acetamidophenoxy)-3-{N-[2-(4-acetamidophenoxy)ethyl]-N-benzylamino}propan-2-ol is converted to 1-(4-acetamidophenoxy)-3-N-[2-(4-acetamidophenoxy)ethylamino]-2propionoxypropane on treatment with propionic acid anhydride in the presence of pyridine, followed by hydrogenolysis; and 1-(4-acetamidomethylphenoxy)-3-{N-[2-(4-acetamidophenoxy)ethyl]-N-benzylamino}propan-2-ol is converted to 1-(4-acetamidomethylphenoxy)-3-N-[2-(4acetamidophenoxy)ethylamino]-2-(n-capronoxy)propane on treatment with caproic acid anhydride in the presence of pyridine, followed by hydrogenolysis. Other esters of this invention (i.e., compounds where R₂ in the structural formula is alkanoyl as previously defined) are similarly prepared.

EXAMPLE XV

The non-toxic hydrohalide acid addition salts of each of the 1-phenylthio: and 1-phenoxy-3-alkylaminopropan-2-ol base compounds of this invention reported previously, such as the corresponding hydrochloride, hydrobromide and hydriodide salts, are each individually prepared by first dissolving the respective organic base compound in absolute ether and then adding a saturated solution of the appropriate hydrohalide gas in ethyl acetate to the aforementioned ethereal solution, whereupon the desired acid addition salt soon precipitates from said solution. In this way, 5.0 g. of 1-(2-methyl-4-acetamidophenoxy)-3-[2-(4-acetamidophenoxy)ethylamino]propan-2-ol, reported in Example VIII (as a free base compound), is converted via dry hydrogen chloride gas to the corresponding hydrochloride acid addition salt in almost quantitative yield.

EXAMPLE XVI

The nitrate, sulfate or bisulfate, phosphate or acid phosphate, acetate, maleate, fumarate, lactate, tartrate, citrate, gluconate, saccharate, methanesulfonate, benzenesulfonate and p-toluenesulfonate salts of each of the aforementioned 1-phenylthio- and 1-phenoxy-3-alkylaminopropan-2-ol base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition salt therefrom. In this manner, equimolar amounts of 1-(2-methyl-4-acetamidophenoxy)-3-[2-(4-acetamidophenoxy)ethylamino]propan-2ol and concentrated sulfuric acid react to afford the corresponding sulfuric acid addition salt. In like manner, each of the other salts is also similarly prepared.

What is claimed is:

1. A method for effecting anti-anginal action in the treatment of a cardiac-afflicted subject, which comprises administering to said subject an effective anti-anginal amount of a compound selected from the group consisting of phenoxypropanolamine bases of the formula:

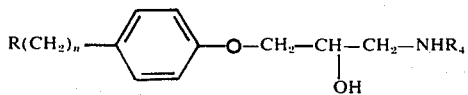

and the pharmaceutically acceptable acid addition salts thereof, wherein R of $R(CH_2)_n$ is alkanoylamino having from one to six carbon atoms when n is zero and is alkanoylamino having from one to three carbon atoms when n is one, said $n$ being an integer of from 0 to 1, inclusive; $R_1$ is hydrogen, allyl or methyl, and $R_4$ is alkanoylaminophenoxyethyl having from one to six carbon atoms in the alkanoyl moiety.

2. The method as claimed in claim 1 wherein the compound administered is 1-(4-acetamidophenoxy)-3-[2-(4-acetamidophenoxy)ethylamino]propan-2ol.

3. The method as claimed in claim 1 wherein the compound administered is 1-(4-acetamidomethylphenoxy)-3-[2-(4-acetamidophenoxy)ethylamino]propan-2-ol.

4. The method as claimed in claim 1 wherein the compound administered is 1-(2-methyl-4-acetamidophenoxy)-3-[2-(4-acetamidophenoxy)ethylamino]propan-2-ol.

5. The method as claimed in claim 1 wherein the compound administered is 1-(2-methyl-4-acetamidomethylphenoxy)-3-[2-(4-acetamidophenoxy)ethylamino]propan-2-ol.

6. The method as claimed in claim 1 wherein the compound administered is 1-(2-allyl-4-acetamidophenoxy)-3-[2-(4-acetamidophenoxy)ethylamino]propan-2-ol.

* * * * *